United States Patent [19]

Richardson et al.

[11] Patent Number: 4,466,974
[45] Date of Patent: Aug. 21, 1984

[54] BISTRIAZOLE ANTIFUNGAL AGENTS

[75] Inventors: Kenneth Richardson, Canterbury; Kelvin Cooper, Ramsgate, both of England

[73] Assignee: Pfizer Inc., New York, N.Y.

[21] Appl. No.: 547,267

[22] Filed: Oct. 31, 1983

[30] Foreign Application Priority Data

Nov. 16, 1982 [GB] United Kingdom ............... 8232705

[51] Int. Cl.$^3$ ..................... A01N 43/64; A01N 47/12; A61K 31/41; C07D 249/08
[52] U.S. Cl. .................................. 424/269; 548/262; 548/239; 548/112
[58] Field of Search ....................... 548/262; 424/269

[56] References Cited

U.S. PATENT DOCUMENTS 4,404,216  9/1983  Richardson ........................ 548/262
4,416,682 11/1983  Worthington ..................... 548/262

FOREIGN PATENT DOCUMENTS 2908378  9/1980  Fed. Rep. of Germany ...... 424/269
2078719  1/1982  United Kingdom ............... 548/262

Primary Examiner—Alton D. Rollins
Attorney, Agent, or Firm—Charles J. Knuth; Albert E. Frost; James M. McManus

[57] ABSTRACT

Compounds of the formula

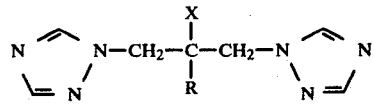

wherein X is an amine function and R is substituted phenyl and their pharmaceutically acceptable salts are useful antifungal agents in animals, including man.

9 Claims, No Drawings

BISTRIAZOLE ANTIFUNGAL AGENTS

BACKGROUND OF THE INVENTION

This invention relates to novel triazole derivatives which have antifungal activity and are useful in the treatment of fungal infections in animals, including humans, and as agricultural fungicides.

U.K. patent application No. 2,078,719A discloses and claims a series of 1,3-bis-(1,2,4-triazolyl)-2-substituted-2-propan-2-ols as antifungal agents.

Belgian Pat. No. 890,741 discloses as antimycotic agents a group of N-(2-chloro-2,3-disubstituted-propyl)-imidazoles.

SUMMARY OF THE INVENTION

The compounds of the present invention are of the formula

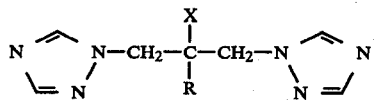
(I)

and the pharmaceutically acceptable acid addition salts thereof, where X is amino, dialkylamino said alkyl having from one to three carbon atoms or alkoxycarbonylamino said alkoxy having from one to three carbon atoms and R is dichlorophenyl.

A preferred group of compounds are those where R is 2,4-dichlorophenyl; especially preferred is 2-amino-1,3-bis(1H-1,2,4-triazol-1-yl)-2-(2,4-dichlorophenyl)-propane, 1,3-bis(1H-1,2,4-triazol-1-yl)-2-(2,4-dichlorophenyl)-2-(N,N-dimethylamino)propane and 1,3-bis-(1H-1,2,4-triazol-1-yl)-2-(2,4-dichlorophenyl)-2-methoxy-carbonylaminopropane.

The invention also provides a pharmaceutical composition comprising a compound of the formula (I) or a pharmaceutically acceptable salt thereof, together with a pharmaceutically acceptable diluent or carrier.

The invention further provides a compound of the formula (I) or a pharmaceutically acceptable salt thereof, for use in medicine, in particular for use in treating a fungal infection in a human being.

The invention yet further provides a composition for use as an agricultural fungicide, comprising a compound of the formula (I) or an agriculturally acceptable salt thereof, together with an agriculturally acceptable diluent or carrier.

The invention yet further provides a method of treating a plant or seed having a fungal infection, which comprises treating said plant or seed, or the locus of said plant, with an antifungally effective amount of a compound of the formula (I) or agriculturally acceptable salt thereof.

DETAILED DESCRIPTION OF THE INVENTION

The compounds of the formula (I) can be prepared as follows:

(1) The compounds of the formula (I) in which X is $-NH_2$ can be prepared by the following general reaction:

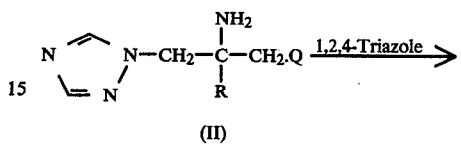
(II)

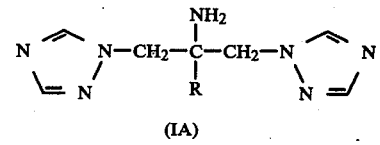
(IA)

Q is a facile leaving group, such as Cl, Br, I, methanesulphonyloxy, trifluoromethanesulphonyloxy ($CF_3SO_2.O-$) or p-toluenesulphonyloxy.

The compounds of the formula (II) can be prepared by conventional means from the corresponding hydroxycompounds of the formula (III):

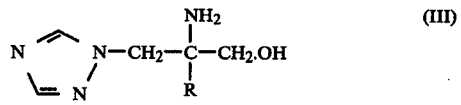
(III)

using e.g. $SOCl_2$, $SOBr_2$, mehtanesulphonyl chloride, methyl triphenoxyphosphonium trifluoromethane sulphonate [$(PhO)_3P^{\oplus}CH_3.CF_3SO_2O^{\ominus}$] or p-toluenesulphonyl chloride. Compounds in which Q is I are typically prepared by reaction of compounds in which Q is Cl with KI.

A particularly suitable leaving group is trifluoromethanesulphonyloxy, the starting materials (II) being preparable in situ from compound (III) and methyl triphenoxyphosphonium trifluoromethane sulphonate. Thus the compounds (IA) are typically prepared by heating compound (III), said sulphonate and 1,2,4-triazole in a suitable organic solvent, e.g. dry tetrahydrofuran, at up to reflux temperature, for up to about 36 hours. The product (IA) can be recovered and purified by conventional methods.

The starting materials (III) are typically prepared by the following route:

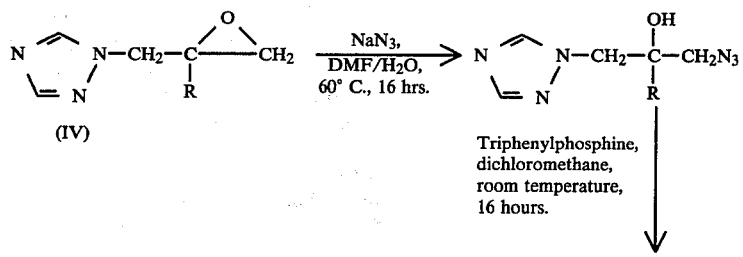
(IV)

Triphenylphosphine,
dichloromethane,
room temperature,
16 hours.

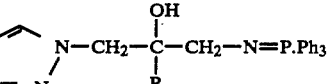
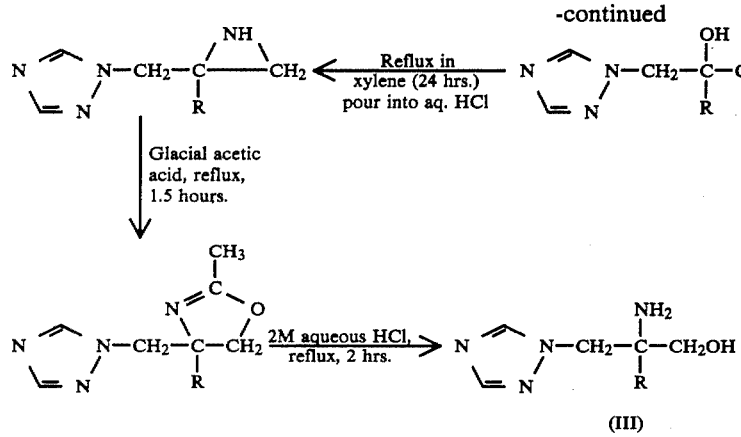
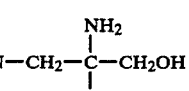
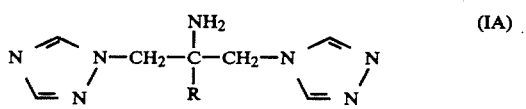
(III)

These reactions are described in detail in the following Preparation.

The starting materials (IV) are either known compounds (see e.g. U.K. patent application publication No. 2078719A) or can be made by conventional procedures. A typical route is as follows:

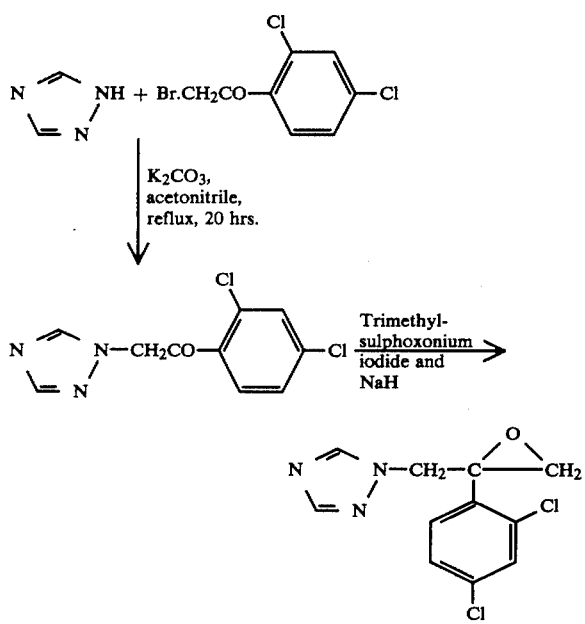

(2) Compounds of the formula (I) in which X is dialkylamino can be prepared by the alkylation of the corresponding free amino compounds of the formula (IA):

according to conventional techniques.

The preferred method of alkylation is to react compound (IA) with at least two equivalents of the appropriate aldehyde in the presence of a suitable reducing agent, e.g. sodium cyano borohydride.

The reaction is typically carried out by stirring the borohydride, compound (IA) and appropriate amount of aldehyde in a suitable organic solvent, e.g. acetonitrile, at room temperature for a few hours. Generally the reaction mixture should be kept acid by the addition of e.g. glacial acetic acid. If necessary, the reaction can be accelerated by heating. The product can then be isolated and purified conventionally.

(3) Compounds of the formula (I) in which X is alkoxy-carbonylamino can be prepared by the reaction of the corresponding compounds in which X is —NH$_2$ [formula (IA)] with an alkyl chloroformate, preferably in the presence of a base. Alternatively, the compound (IA) can be reacted with a strong base such as sodium hydride to generate the —NH$^\ominus$ anion, followed by reaction with an alkyl chloroformate. This is in fact preferred.

Thus in a typical procedure the compound (IA) and sodium hydride are stirred together at room temperature in a suitable organic solvent, e.g. tetrahydrofuran, for about 1 hour, and the alkyl chloroformate is then added and the reaction mixture stirred for up to about a further 24 hours at room temperature. Heating may in some cases be necessary to accelerate the reaction.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing approximately equimolar amounts of the free base and desired acid, and the required salt is collected by filtration, if insoluble, or by evaporation of the solvent.

The compounds of the formula (I) and their pharmaceutically acceptable salts are antifungal agents, useful in combating fungal infections in animals, including humans. For example they are useful in treating topical fungal infections in man caused by, among other organisms, species of *Candida, Trichophyton, Microsporum* or *Epidermophyton,* or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus fumigatus, Coccidioides, Paracoccidioides, Histoplasma,* or *Blastomyces.*

The in vitro evaluation of the antifungal activity of the compounds can be performed by determining the minimum inhibitory concentration (m.i.c.) of the test compounds in a suitable medium at which growth of the particular micro-organism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Cryptococcus neoformans, Aspergillus fumigatus, Trichophyton* spp; *Microsporum* spp; *Epidermophyton floccosum, Coccidioides immitis* and *Torulopsis glabrata.*

The in vivo evaluation of the compounds can be carried out at a series of dose levels by intraperitoneal or intravenous injection or by oral administration, to mice which are inoculated with a strain of *Candida albicans.* Activity is based on the survival of a treated group of mice after the death of an untreated group of mice following 48 hours observation. The dose level at which the compound provides 50% protection against the lethal effect of the infection is noted.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated in a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including, for example, various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerella cingulata, Penicillium digitatum, Botrytis cinerea* and *Rhizoctonia solani.*

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways; for example, they can be applied directly to the plant foliage, stems, branches, seeds or roots or to the soil or other growing medium, and they may be used not only to eradicate disease, but also prophylactically to protect the plants or seeds from attack.

The following Examples illustrate the invention. All temperatures are in ° C.

EXAMPLE 1

Preparation of 2-amino-1,3-bis(1H-1,2,4-triazol-1-yl)-2-(2,4-dichlorophenyl)propane A solution of 2-amino-2-(2,4-dichlorophenyl-3-(1H-1,2,4-triazol-1yl)-propan-1-yl (7.8 g, 27.2 mmole), methyl triphenoxyphosphonium trifluoromethane sulphonate (16.72 g, 35.2 mmole) and 1,2,4-triazole (10.56 g, 153 mmole) in dry tetrahydrofuran (400 ml) was heated at reflux for 28 hours. The solution was then cooled and the solvent removed in vacuo. The residue was taken up in dichloromethane and was then washed with 10% aqueous sodium carbonate solution (100 ml). The organic phase was dried ($MgSO_4$), filtered and evaporated and the residue chromatographed on silica, eluting with chloroform/methanol/ammonia, 350:10:1. The fractions containing the product were evaporated and the residue was recrystallized from ethyl acetate/hexane to afford the amine as a colorless solid (3.2 g, 35%), m.p. 135°-6°.

Analysis %: Found: C, 46.00; H, 3.67; N, 29.18 Calculated for $C_{13}H_{13}Cl_2N_7$: C, 46.16; H, 3,87; N, 28.99.

EXAMPLE 2

Preparation of 1,3-bis(1H-1,2,4-triazol-1-yl)-2-(2,4-dichlorophenyl)-2-(N-N-dimethylamino)propane, dihydrochloride hemihydrate Sodium cyanoborohydride (0.28 g, 4.5 mmole) was added to a mixture of 2-amino-1,3-bis(1H-1,2,4-triazol-1-yl)-2-(2,4-dichlorophenyl)propane (0.273 g, 0.8 mmole) and 37% aqueous formaldehyde (1.2 ml, 15 mmole) in acetonitrile (12 ml). The mixture was stirred at room temperature for 2 hours keeping the mixture acid (pH 4) by the addition of glacial acetic acid. The mixture was diluted with ether (25 ml) and washed with 2M sodium hydroxide solution (10 ml) followed by saturated sodium chloride solution (10 ml). The organic phase was dried ($MgSO_4$), filtered and evaporated and the residue was chromatographed on silica eluting with ethyl acetate. The fractions containing the product were evaporated and the residue was converted to its hydrochloride by dissolving it in dichloromethane and adding ethereal hydrogen chloride. The reaction mixture was evaporated in vacuo and the hydrochloride residue was then recrystallized from a diethyl ether-methanol mixture to afford the title dihydrochloride as a colorless solid, (74 mg, 20%), m.p. 195°–8°.

Analysis %: Found: C, 40.52; H, 4.78; N, 22.16 Calculated for $C_{15}H_{17}Cl_2N_7 \cdot 2HCl \cdot \frac{1}{2}H_2O$ C, 40.2; H, 4.5; N, 21.88.

EXAMPLE 3

Preparation of 1,3-bis-(1H-1,2,4-triazol-1-yl) 2-(2,4-dichlorophenyl)-2-methoxycarbonylaminopropane hemihydrate 2-Amino-1,3-bis(1H-1,2,4-triazol-1-yl)-2-(2,4-dichlorophenyl)propane (0.234 g, 0.7 mmole) was added to a suspension of oil-free sodium hydride (27 mg, 1.125 mmole) in dry tetrahydrofuran (5 ml) and the mixture was stirred at room temperature for 1 hour. Methyl chloroformate (0.104 g, 1.1 mmole) was then added and the mixture was stirred at room temperature for 16 hours. The solvent was removed in vacuo and the residue dissolved in chloroform (25 ml) and then washed with water (10 ml). The organic phase was dried ($MgSO_4$), filtered and evaporated and the residue was recrystallized from ethyl acetate to furnish the title compound as a colorless solid (48 mg, 17%), m.p. 171°–2°.

Analysis %: Found: C, 44.58; H, 3.8; N, 24.62 Calcualted for $C_{15}H_{15}Cl_2N_7O_2 \cdot \frac{1}{2}H_2O$: C, 44.46; H, 3.98; N, 24.19.

EXAMPLE 4

The following illustrate pharmaceutical compositions for the treatment of fungal infections:

(1) Capsule: 71 parts by weight of the compound of Example 1 are granulated with 3 parts maize starch and 22 parts lactose and then a further 3 parts of maize starch and 1 part magnesium stearate are added. The mixture is regranulated and filled into hard gelatin capsules.

(2) Cream: 2 parts by weight of the compound of Example 1 are dissolved in 10 parts of propylene glycol and mixed into 88 parts of a vanishing cream base.

(3) Pessary: 2 parts by weight of the compound of Example 1 are suspended in 98 parts of a warm liquified suppository base which is poured into moulds and allowed to solidify.

Using the test method described in the text, the following $PD_{50}$ values (mg/kg) were obtained in mice infected with *Candida albicans*:
Product of Example 1 $PD_{50}$ (mg/kg) = 1.5;
Product of Example 2 $PD_{50}$ (mg/kg) = ~20;
Product of Example 3 $PD_{50}$ (mg/kg) = 3.1.

The following Preparation illustrates the preparation of the starting material used in Example 1. All temperatures are in °C.

PREPARATION SECTION (i) Preparation of 2-(1H-1,2,4-Triazol-1-yl)-2',4'-dichloro acetophenone This compound was prepared similarly to the method described in British patent specification No. 1512918.

(ii) Preparation of 2-(2,4-Dichlorophenyl)-2-(1H-1,2,4-triazol-1-ylmethyl)-oxirane 3.78 g (0.079 Mole) of sodium hydride (50% dispersion in oil) was suspended, with stirring, in 20 ml of dry ether. The ether was then removed by decantation, and the sodium hydride was dried in a stream of dry nitrogen. 100 ml of dry dimethyl sulphoxide was added followed by 17.34 g (0.079 mole) of dry powdered trimethylsulphoxonium iodide, in portions, over 15 minutes. The resulting mixture was stirred for 30 minutes at room temperature (20°). 18.33 g (0.072 mole) of compound (A) as a solution in 50 ml of dry dimethyl sulphoxide was then added. The mixture was heated at 60° for 3 hours and then stood at room temperature overnight. The reaction mixture was cooled and quenched in ice. The product was then extracted into ethyl acetate (600 ml). The ethyl acetate layer was separated, dried over magnesium sulphate, and concentrated to give a red gum. Column chromatography of the gum on silica, eluting with ether, gave the product (B). On evaporation, 6.62 g (34.4%) of the title compound (B) was obtained as a gum which solidified under vacuum. The pure product melted at 57°–59°.

Analysis %: Found: C, 48.6; H, 3.3; N, 15.3 Calculated for $C_{11}H_9Cl_2N_3O$: C, 49.0; H, 3.4; N, 15.5.

The product was converted to the monomesylate salt using methanesulphonic acid in a conventional manner. The monomesylate was used directly in the next stage.

(iii) Preparation of 1-azido-2-(2,4-dichlorophenyl)-3-(1H-1,2,4-triazol-1-yl)propan-2-ol A solution of sodium azide (22.75 g, 0.35 mole) in water (62.5 ml) was added to a solution of 2-(2,4-dichlorophenyl)-2-(1H-1,2,4-triazol-1-ylmethyl)oxirane monomesylate (25 g, 0.068 mole) in dimethylformamide (DMF) (250 ml) and the reaction mixture was stirred at room temperature for 0.5 hours and then at 60° for 16 hours. The reaction mixture was cooled and then poured into a mixture of dichloromethane (250 ml) and water (75 ml). The two phases were separated and the aqueous phase was extracted with dichloromethane (2×25 ml) and the combined organic extracts were then dried ($MgSO_4$), filtered and evaporated. The residue was triturated with diethyl ether and the resulting solid filtered off and then recrystallized from an ethyl acetate-hexane mixture to furnish the title azide as a colorless crystalline solid, (16.9 g, 79%) m.p. 117°–19°.

Analysis %: Found: C, 42.31; H, 3.22; N, 27.07 Calculated for $C_{11}H_{10}Cl_2N_6O$: C, 42.18; H, 3.22; N, 26.83.

(iv) Preparation of N-[2-(2,4-dichlorophenyl)-2-hydroxy-3-(1H-1,2,4-triazol-1-yl)propyl]triphenylphosphinimine Triphenylphosphine (14.15 g, 54 mmole) was added in portions to a stirred solution of 1-azido-2-(2,4-dichlorophenyl)-3-(1H-1,2,4-triazol-1-yl)propan-2-ol (16.9 g, 54 mmole) in dichloromethane (340 ml) and the solution was then stirred at room temperature for 16 hours. The solvent was removed under reduced pressure and the residue was recrystallized from a dichloromethanehexane mixture to afford the title triphenylphosphinimine as a colorless solid, (29.15 g, 98%), m.p. 183°-4°.

Analysis %: Found: C, 63.41; H, 4.59; N, 10.37 Calculated for $C_{29}H_{25}Cl_2N_4OP$: C, 63.6; H, 4.57; N, 10.24.

(v) Preparation of 2-(2,4-dichlorophenyl)-2-(1H-1,2,4-triazol-1-ylmethyl)aziridine A solution of N-[2-(2,4-dichlorophenyl)-2-hydroxy-3-(1H-1,2,4-triazol-1-yl)propyl]triphenylphosphinimine (31.65 g, 57.8 mmole) in xylene (210 ml) was heated at reflux for 24 hours. The solution was then cooled and poured into 2M hydrochloric acid (300 ml) and the organic phase was separated and re-extracted with 2M hydrochloric acid (3×50 ml). The aqueous extracts were combined and then basified (pH 8) with solid sodium bicarbonate and then extracted with dichloromethane (3×100 ml). The organic phase was separated, dried ($MgSO_4$), filtered and evaporated to leave the title aziridine as a pale green gum (14.5 g, 93%). The product was characterized by n.m.r., i.r. and mass spectroscopy: it was unstable and was used directly in the next stage.

(vi) Preparation of 4-(2,4-dichlorophenyl)-2-methyl-4-(1H-1,2,4-triazol-1-ylmethyl)oxazol-2-ine A solution of 2-(2,4-dichlorophenyl)-2-(1H-1,2,4-triazol-1-ylmethyl)aziridine (14.05 g, 52.2 mmole) in glacial acetic acid (140 ml) was heated at reflux for 1.5 hours. The acetic acid was removed under vacuum and the residue was then dissolved in chloroform (100 ml). The chloroform solution was washed with saturated sodium bicarbonate solution (25 ml) followed by saturated aqueous sodium chloride solution (25 ml) and then dried ($MgSO_4$), filtered, and evaporated to leave the crude product. The crude product was chromatographed on silica eluting with ethyl acetate. The fractions containing the product were evaporated and the residue was recrystallized from an ethyl acetate/hexane mixture to yield the title oxazoline as a colorless crystalline solid (11 g, 68%), m.p. 100°101°.

Analysis %: Found: C, 49.87: H, 3.85; N, 18.35 Calculated for $C_{13}H_{12}Cl_2N_4O$: C, 50.16; H, 3.85; N, 18:0.

(vii) Preparation of 2-amino-2-(2,4-dichlorophenyl)-3-(1H-1,2,4-triazol-1-yl)propan-1-ol A solution of 4-(2,4-dichlorophenyl)-2-methyl-4-(1H-1,2,4-triazol-1-ylmethyl)oxazol-2-ine (10.9 g, 35 mmole) in 2M hydrochloric acid (200) was heated at reflux for 2 hours. The solution was cooled and then basified (pH 10) with solid sodium carbonate. The aqueous mixture was extracted with ethyl acetate (3×150 ml) and the combined organic extracts were dried ($MgSO_4$), filtered and evaporated, and the residue was recrystallized from an ethyl acetate/hexane mixture to furnish the title aminoalcohol as a colorless crystalline solid, (8.8 g, 88%), m.p. 131°133°.

Analysis %: Found: C, 46.07; H, 4.14; N, 19.84 Calulated for $C_{11}H_{12}Cl_2N_4O$: C, 45.99; H, 4.18; N, 19.5.

We claim:

1. A compound having the formula

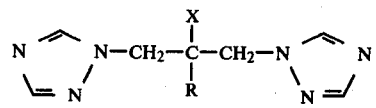

and the pharmaceutically acceptable acid addition salts thereof wherein X is selected from the group consisting of amino, dialkylamino wherein said alkyl contains from one to three carbon atoms and alkoxycarbonylamino wherein said alkoxy contains from one to three carbon atoms; and R is dichlorophenyl.

2. A compound of claim 1, wherein R is 2,4-dichlorophenyl.

3. The compound of claim 2, wherein X is amino.

4. The compound of claim 2, wherein X is dimethylamino.

5. The compound of claim 2, wherein X is methoxycarbonylamino.

6. A pharmaceutical composition comprising a compound as claimed in claim 1, together with a pharmaceutically acceptable diluent or carrier.

7. A method of treating a fungal infection in a human being, which comprises administering to said human an antifungal amount of a compound as claimed in claim 1.

8. A plant or seed antifungal composition comprising a compound as claimed in claim 1, together with a agriculturally acceptable diluent or carrier.

9. A method for treating a plant or seed having a fungal infection, which comprises administering to said plant or seed an antifungal amount of a compound as claimed in claim 1.

* * * * *